US00PP21184P3

(12) United States Plant Patent

Yamazaki et al.

(10) Patent No.: US PP21,184 P3

(45) Date of Patent: Aug. 3, 2010

(54) BUNASHIMEJI MUSHROOM PLANT NAMED 'HOKUTO-18'

(50) Latin Name: *Hypsizigus marmoreus*
Varietal Denomination: Hokuto-18

(75) Inventors: Mizue Yamazaki, Nagano (JP); Takeshi Oku, Kishiwada (JP); Satoshi Inatomi, Nagano (JP); Kenji Namba, Nagano (JP)

(73) Assignee: Hokuto Co., Ltd., Nagano (JP)

( * ) Notice: Subject to any disclaimer, the term of this patent is extended or adjusted under 35 U.S.C. 154(b) by 894 days.

(21) Appl. No.: 11/206,202

(22) Filed: Aug. 18, 2005

(65) Prior Publication Data

US 2006/0041984 P1 Feb. 23, 2006

(30) Foreign Application Priority Data

Aug. 19, 2004 (JP) ..... 17353

(51) Int. Cl.
*A01H 5/00* (2006.01)

(52) U.S. Cl. ..... Plt./394

(58) Field of Classification Search ..... Plt./394
See application file for complete search history.

(56) References Cited

U.S. PATENT DOCUMENTS

2006/0041984 P1 * 2/2006 Yamazaki et al. ..... Plt./394

* cited by examiner

*Primary Examiner*—Annette H Para
(74) *Attorney, Agent, or Firm*—Kratz, Quintos & Hanson, LLP

(57) ABSTRACT

A new and distinct variety of mushroom plant of Bunashimeji mushroom, *Hypsizigus marmoreus*, named 'Hokuto-18', is cultivated by gathering and repeated breeding of fungal strains having dominant traits. This new and distinct variety has good qualitative character and appearance, good keeping quality and storage life and delicious tasting and is exquisite in stability, reproducibility and uniformity when being produced.

10 Drawing Sheets

Latin name of the genus and species of the plant claimed: *Hypsizigus marmoreus*.

BACKGROUND OF THE INVENTION

This invention relates to a new and distinct variety of mushroom plant of Bunashimeji mushroom, *Hypsizigus marmoreus*. This new variety named 'Hokuto-18' cultivated by repeated breeding of Bunashimeji mushrooms having dominant traits, which is tasty and less bitter to the taste, has excellent quality, pleasing appearance, good keeping quality and storage life and ensure stability, reproducibility and uniformity.

Whereas the Bunashimeji mushroom has been so far cultivated artificially and widely eaten, the Bunashimeji mushroom produced by gathering and artificially cultivating wild mushrooms tastes unpleasantly bitter.

The Bunashimeji mushroom has a cap (pileus) with mottles. The mottles of the artificially cultivated Bunashimeji mushroom take various forms such as clear mottles, minute mottles or dilute mottles. The fine mottles, which are characteristic of the Bunashimeji mushroom, improve the appearance of the mushroom and prove to be good in quality. The thicknesses of the stem and cap of the mushroom affect eating quality. It is of course that the mushroom having good eating quality is superior in quality of goods. It is therefore significant to find suitable varieties of mushroom out of wild Bunashimeji mushrooms in order to improve the varieties as much as possible.

Furthermore, the perishable mushroom gradually deteriorates in flavor and quality when being preserved for a while after harvesting. Thus, there has been a need for mushrooms having good keeping quality and storage life so as not to degrade their quality during the course of distribution. However, it is disadvantageously difficult to find suitable fungal strains having good qualitative character and high quality from a huge variety of wild mushrooms gathered and screened carefully.

SUMMARY OF THE INVENTION

The present invention is a new and distinct variety of mushroom characterized particularly by its good qualitative character and appearance, good keeping quality and storage life and delicious tasting, which can be cultivated by gathering and repeated breeding of fungal strains having dominant traits and is exquisite in stability, reproducibility and uniformity when being produced. This novel and distinct variety of mushroom is identified as 'Hokuto-18'.

BOTANICAL DESCRIPTION

Figure 1A:
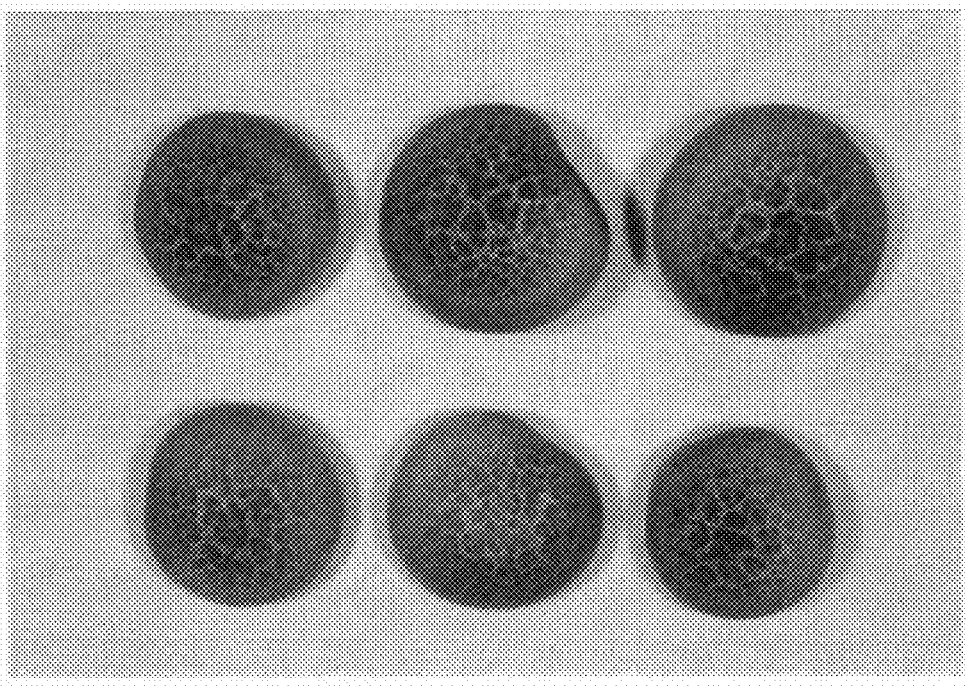
FIG. 1A shows a top view of new variety of mushrooms named 'Hokuto-18' of the present invention.
Figure 1B:
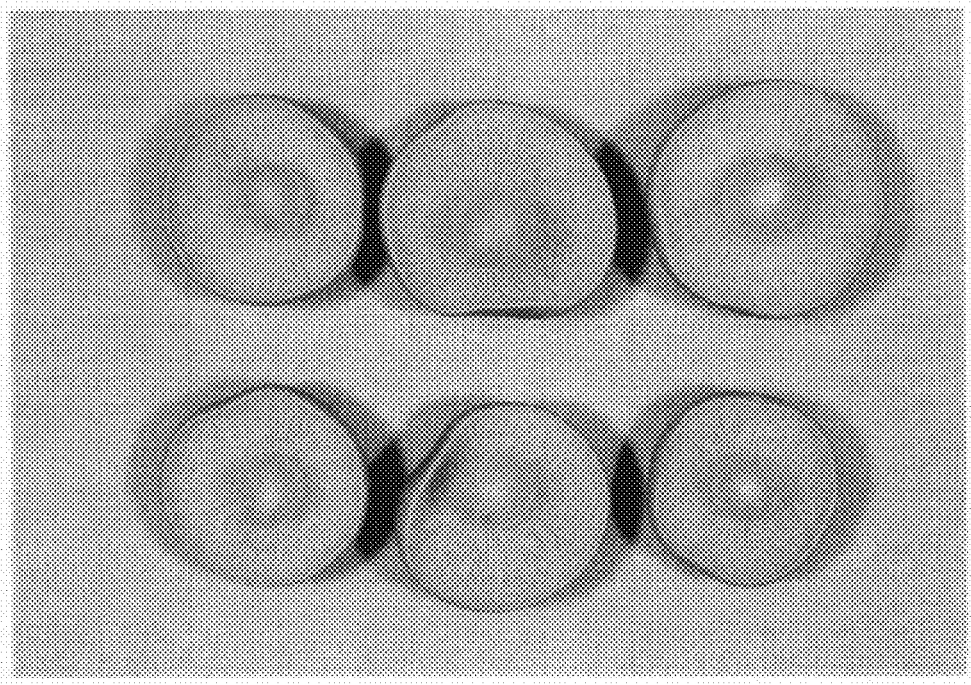
FIG. 1B shows a bottom view of the mushrooms of FIG. 1A.
Figure 1C:
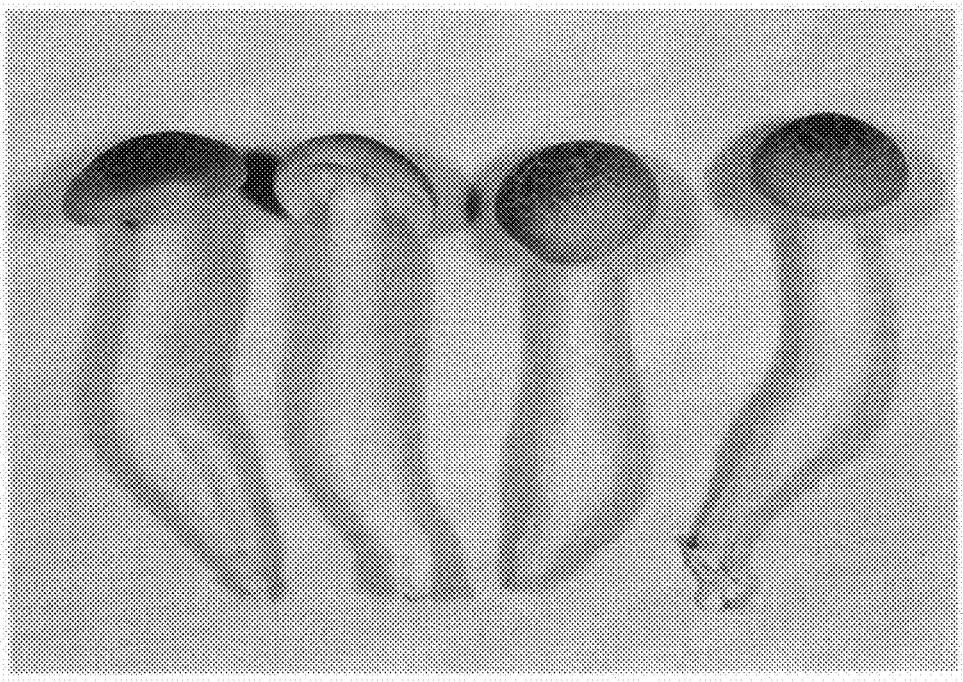
FIG. 1C shows a side view of the mushrooms of FIG. 1A.
Figure 1D:
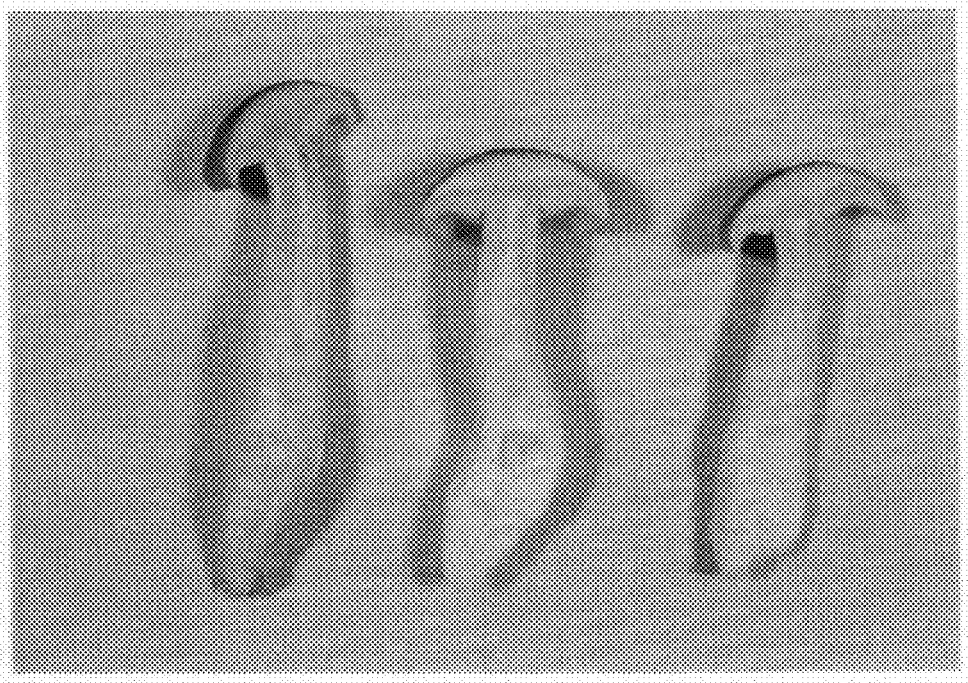
FIG. 1D shows a side cutaway view of the mushrooms of FIG. 1A.
Figure 2A:
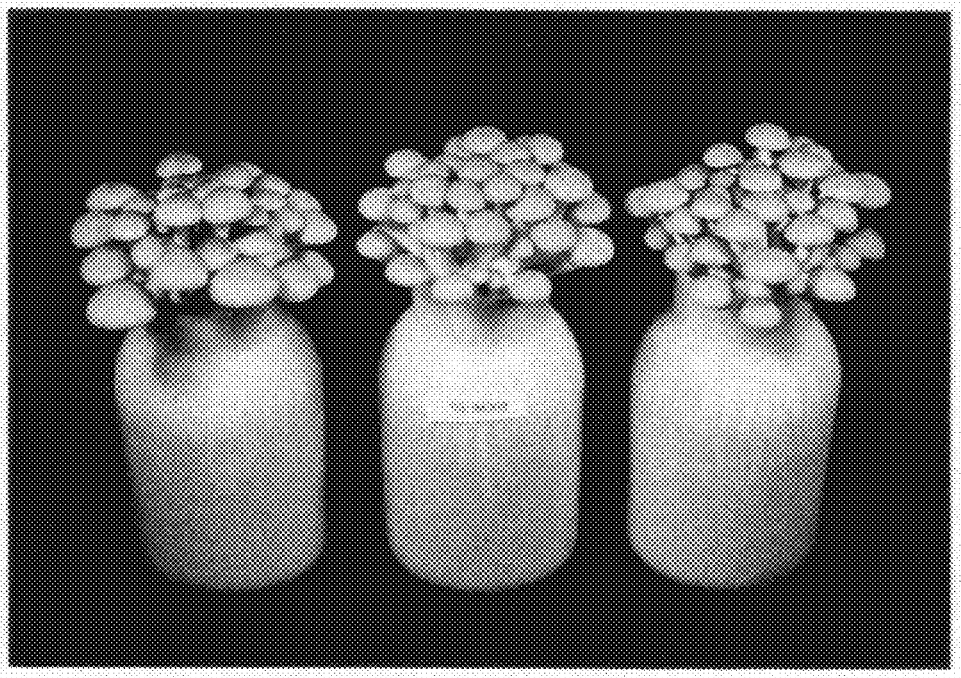
FIG. 2A shows the state of cultivating the 'Hokuto-18' mushrooms in bottles.
Figure 2B:
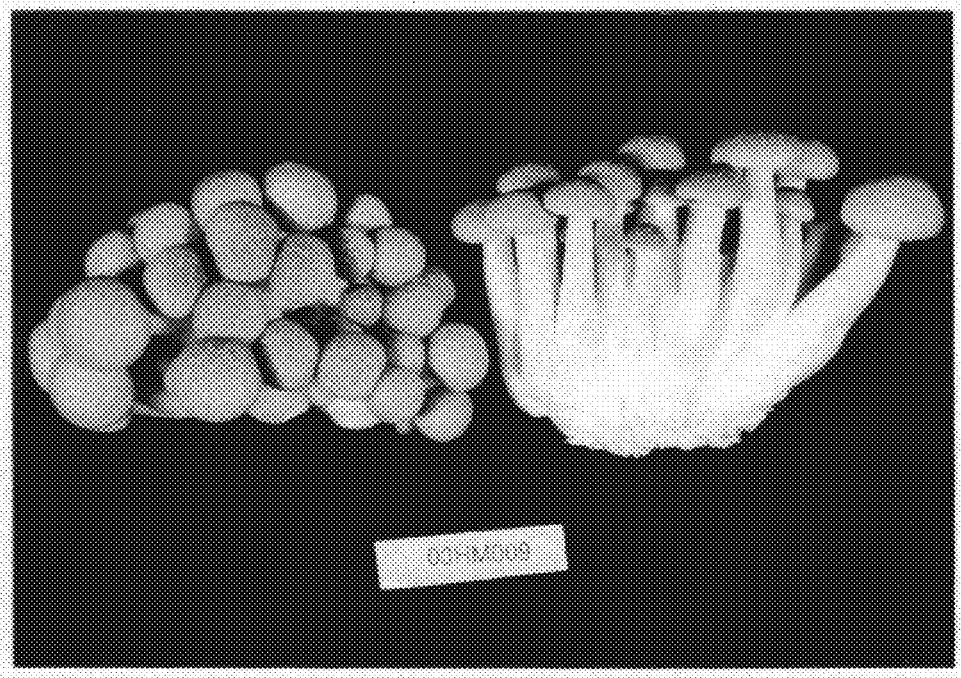
FIG. 2B shows the 'Hokuto-18' mushrooms according to the invention.
Figure 3:
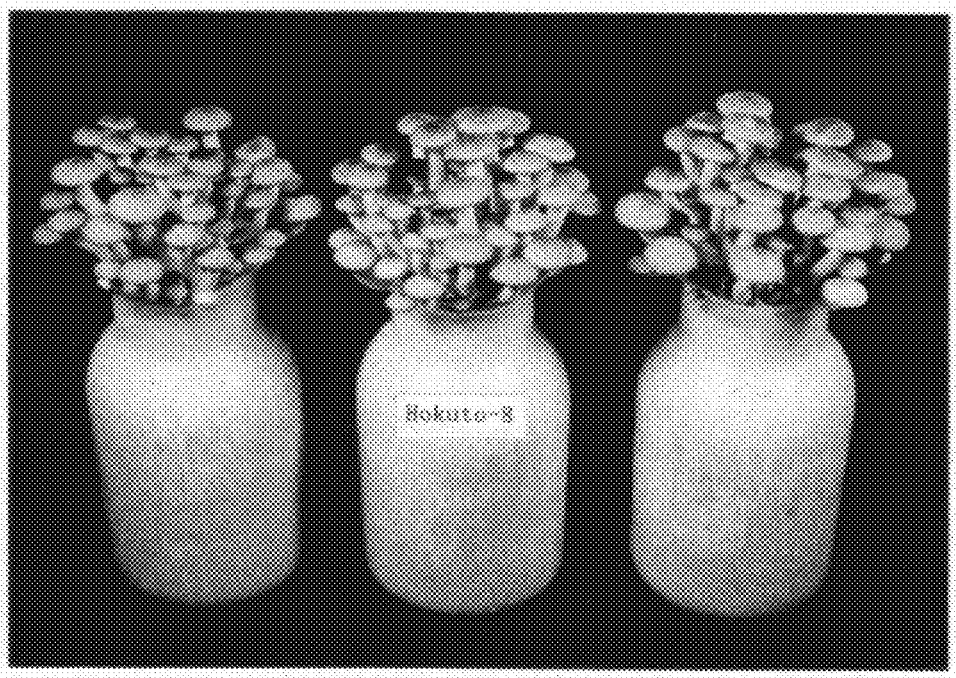
FIG. 3 shows the state of cultivating in bottles a control variety 'Hokuto-8' similar to the mushrooms of the invention.
Figure 4:
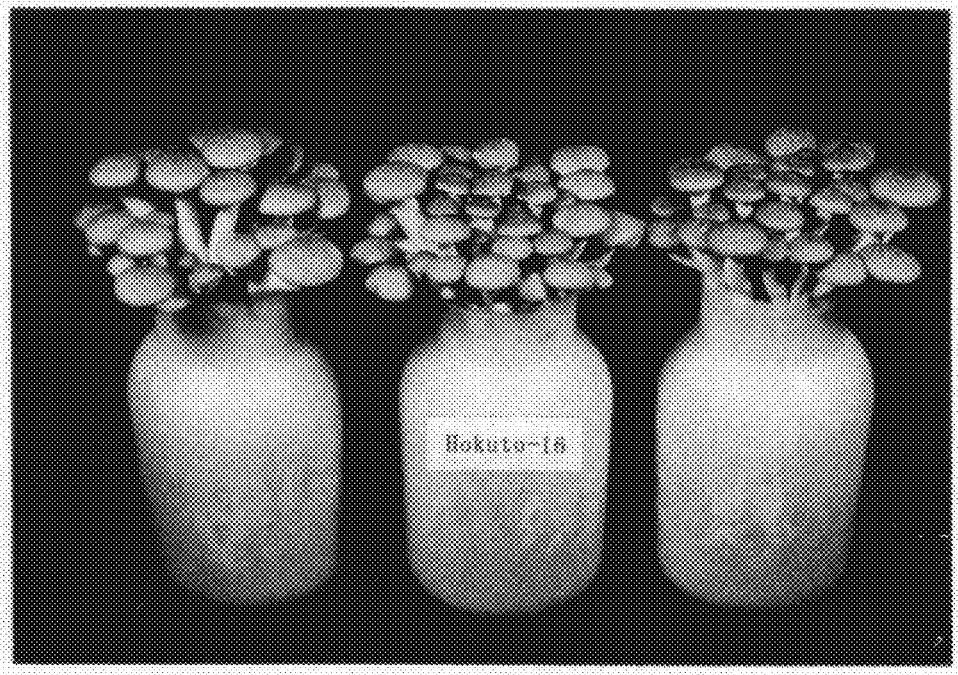
FIG. 4 shows the state of cultivating in bottles a control variety 'Hokuto-16' similar to the mushrooms of the invention.

This invention relates to a new and distinct variety of mushroom plant of Bunashimeji mushroom, *Hypsizigus marmoreus*, named 'Hokuto-18', which is cultivated by repeatedly breeding Bunashimeji mushrooms having dominant traits. This new variety of mushroom is very tasty and not bitter, has excellent quality, pleasing appearance, good keeping quality and storage life and ensure stability, reproducibility and uniformity.

The new variety 'Hokuto-18' according to the invention has been deposited at "International Organism Depository" of National Institute of Advanced Industrial Science and Technology under Deposit No. FERM P-20537.

One actual sample of the new variety 'Hokuto-18' of the invention is shown in FIGS. 1A through 1D. Needless to say, this illustrated sample should not be understood as one and only embodiment of the invention because the subject matter of the invention is a plant having an undefined figure. The morphological characteristics of the new variety 'Hokuto-18' of the invention will be described in detail later.

The new variety 'Hokuto-18' of the invention is produced from two parental cultivars, each cultivated by repeatedly breeding Bunashimeji mushrooms. One of the parental cultivars was produced and uniquely named 'Hokuto Jyurokugokin' ('Hokuto-16'), and another cultivar is white Bunashimeji mushrooms, which was likewise produced and uniquely named 'Hokuto Shiro Ichigoukin'.

The parental cultivar 'Hokuto-16' was obtained by breeding of 'Hokuto Jyuichigokin' ('Hokuto-11'), which has been registered in the Japanese Plant Variety Register under Variety Registration No. 12049 on Mar. 15, 2004, and fungal strains uniquely code-named 'MH025143'. 'Hokuto-16' has not been patented in the United States.

The 'Hokuto Shiro Ichigoukin' was obtained by breeding of a variety 'Hokuto Hachigoukin' ('Hokuto-8'), which was once registered in the Japanese Plant Variety Register, and a variety 'Hokuto Jyunigoukin' ('Hokuto-12') registered in the Japanese Plant Variety Register under Variety Registration No. 10749 and exposing the varieties thus bred to ultraviolet rays to consequently turn whiter or lighter. The 'Hokuto Shiro Ichigoukin' has been registered in the Japanese Plant Variety Register under Variety Registration No. 13294. This variety has been applied for a United States patent and published under No. 20040025215, now plant patent 16,294, issued Feb. 28, 2006.

The processes of breeding and cultivating 'Hokuto-18' according to the invention will be described hereinafter.

[Breeding Process of 'Hokuto-18'].

First, four kinds of Bunashimeji mushrooms gathered in Japan were crossed repeatedly to produce the aforementioned 'Hokuto-16' and white Bunashimeji mushrooms 'Hokuto Shiro Ichigoukin' before October 2001.

The 'Hokuto-16' has good morphological characters, i.e. fleshy stem and cap, clear mottles and good quality, but it has poor keeping quality. Meanwhile, the white Bunashimeji mushroom is superior in quality and keeping quality and storage life and different in whiteness from existing Bunashimeji mushrooms.

Crossbreeding of 'Hokuto-16' and white Bunashimeji mushrooms was performed to develop 628 new breed strains of mushrooms in April 2003. Then, cultivation experiments were carried out for verifying the trait characters of these breed strains thus developed in October 2003, consequently to chase up adequate fungal strains (named '03HM009') having good quality, taste and keeping quality.

Thereafter, further cultivation experiments were repeatedly carried out starting from December 2003 for corroborating stability, reproducibility and uniformity of the new strains, and as a result, proved confirmation that the new fungal strains were fit for the expected purpose of the invention, thus to be named 'Hokuto-18' strains ultimately. The new fungal strain 'Hokuto-18' has been applied for a plant variety registration under the Japanese Seeds and Seedlings Law on Aug. 19, 2004 (Application No. 17353).

[Traits of new fungal strain 'Hokuto-18'].

(1) Comparison with existing varieties injuxtapositional cultivation:

Juxtapositional cultivation experiments were performed several times, placing the parental cultivar of 'Hokuto-18' strain and commercially available varieties in juxtaposition with each other, for observing the reluctant reaction caused when the fungal strains are extraneous to each other. As a result, the juxtapositional cultivation experiments have shown that the parental cultivar of 'Hokuto-18' was extraneous to all the existing varieties (see Table 1 below).

TABLE 1

| Results of juxtapositional cultivation experiments | | | | |
|---|---|---|---|---|
| | | | Control varieties available in the market | |
| | Similar control varieties | | Nagano-grown | Niigata-grown |
| | 'Hokuto-16' | 'Hokuto-8' | variety | variety |
| 'Hokuto-18' | + | + | + | + |

The variety 'Hokuto-8' shown in Table 1 was cultivated by breeding of two fungal strains naturally grown in a mountain in Nagano of Japan in March 1992.

The control variety, Bunashimeji mushroom, grown in Nagano of Japan was commercially available from a supermarket in Japan. Another control variety, Bunashimeji mushroom, grown in Niigata of Japan was also commercially available from a supermarket in Japan.

The experiments for the aforementioned reluctant reaction were performed by inoculating the 'Hokuto-18' strains and the control strains on a potato dextrose agar medium with a distance of 3 centimeters. After conducting the cultivation at 25° C. for 28 days, the reluctant reaction of the testing strains was measured. The results of the experiments for the reluctant reaction confirmed that the 'Hokuto-18' of the invention is new and distinct.

The state of cultivating the 'Hokuto-18' mushrooms in bottles is shown in FIGS. 2A, 2B, 3 and 4.

(2) Cultural characteristics of 'Hokuto-18'.

(a) When the 'Hokuto-18' strain was cultivated on a malt extract agar medium, it was roundly grown so that the fungal threads thereof were grown to 36.98 mm for ten days. The 'Hokuto-18' strain resultantly grown has white fungal threads brought up densely with a great number of aerial hyphae.

(b) When the 'Hokuto-18' strain was cultivated on a potato dextrose agar medium, it was roundly grown so that the fungal threads thereof were grown to 36.69 mm for ten days. The 'Hokuto-18' strain resultantly grown has white fungal threads brought up densely with a great number of aerial hyphae.

(c) After inoculating the seed fungi of 'Hokuto-18' strain of 5 mm in diameter on the potato dextrose agar medium, the cultivation of the strain was conducted at intervals of 5° C. within 5° C. to 35° C. Measurement of growth of the fungal threads of the strain on the cultivating experiments conducted for 15 days showed much more growth of the fungal threads per day at 25° C.

(3) Morphological characteristics of 'Hokuto-18' cultivated experimentally.

[Cultivation method] The cultivation was conducted using a bottle containing sawdust culture medium. The bottle of polypropylene, having a capacity of 800 cc, was used. The culture medium used in the cultivation was prepared by mixing sawdust of broad leaf tree and cedar as a carrier with rice bran by three to one and adding water to the carrier to 65% of moisture content of the carrier. The culture medium thus prepared was sterilized by heating at a high temperature of 120° C. for 40 minutes under high pressure, and then, cooled to about 20° C. Thereafter, the seed fungi were inoculated on the culture medium thus prepared, and therefore, cultivated at 20° C. for 70 days. (The same culture medium as above was used.) Upon completion of cultivation, fungus scratching on the culture medium and sprouting of the seed fungi were performed at a temperature of 15° C. and at a humidity of 90% to breed fungal strains. After gemmation, the fungal strains thus bred were further nurtured at a temperature of 15° C., at a humidity of 95% and at an illumination intensity of 100 Lux. Then, resultantly grown mushrooms were harvested when the caps thereof reach maturity.

The new variety 'Hokuto-18' grown in the manner as described above has the following trait characteristics. The 'Hokuto-18' has a pileus (cap) with an arched top having a central part of yellow tea color and a peripheral part of isabella color. Distinct mottles are distributed all over the upper surface of the fungous pileus except for the periphery thereof. The gills of the fungus are white and normal. The stem is white, shortish, eccentric to the cap and not hairy and has a medium-sized diameter. Eventually there could be harvested 56 strains having a weight of about 111.1 grams on an average and a length of over 2 centimeters.

The distinct differences in trait characters of the new variety 'Hokuto-18' and most similar variety are shown in Table 2 below:

TABLE 2

Differences in trait between 'Hokuto-18' and similar varieties (Comparison of 'Hokuto-18' with similar control varieties)

| Character | 'Hokuto-18' | 'Hokuto-8' | 'Hokuto-16' |
|---|---|---|---|
| Genetic type of fruit body | Aggregatus form | Aggregatus form | Disparate form |
| Effective number of Stems | 111 | 103 | 125 |
| Yield (grams per strain) | 56 | 66 | 49 |
| Diameter of pileus (mm) | 19.4 | 18.0 | 23.1 |
| Color of central part[1] | Yellow tea | Taupe | Taupe |
| Color of fringe part[1] | Isabella | Pale taupe | Pale taupe |
| Fleshy substance | Middle | Soft | Middle |
| Fleshy thickness (mm) | 5.7 | 5.1 | 6.4 |
| Quantity of mottles | Middle | Many | Middle |
| Size of mottles | Middle | Small | Middle |
| Spread of mottles | Except fringe part | Central part | Except fringe part |
| Clearness of mottles | Clear | Normal | Normal |
| Gill (Color)[1] | White | Whity-yellow | White |
| Stem (Length (mm)) | 41.9 | 42.5 | 56.6 |
| Color[1] | White | Whity-yellow | White |
| Ratio of maximum diameter of stem to diameter just below cap | 1.85 | 2.1 | 1.7 |
| Ratio of cap diameter to stem diameter | 2.35 | 2.16 | 2.45 |

[1]Color chart: Royal Horticultural Society. Fifth Edition

Figure 10:
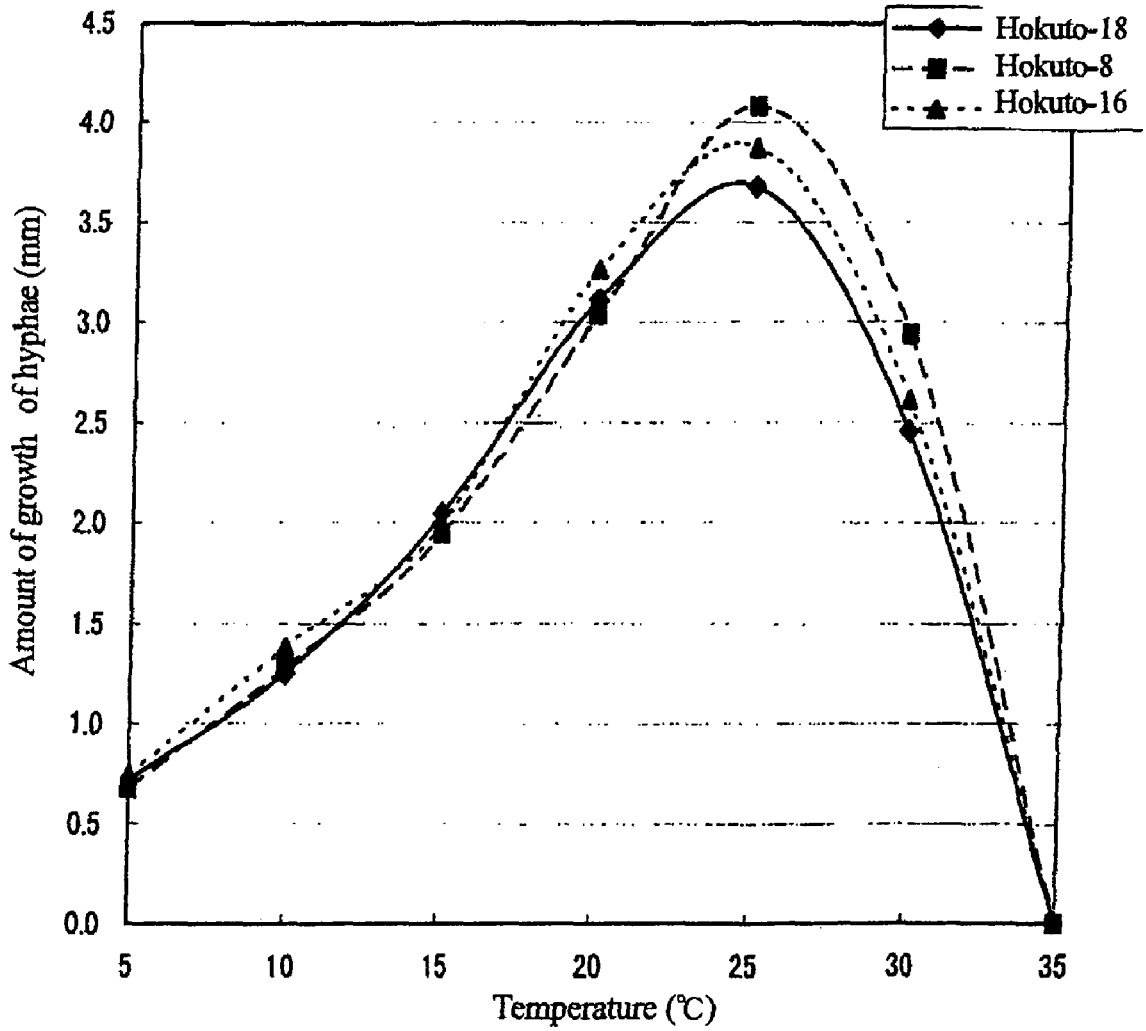
FIG. 10 is a graph showing differences in growth of fungal hyphae among the 'Hokuto-18' mushrooms of the invention and control varieties 'Hokuto-8' and 'HOKUTO-16'.
Figure 11:
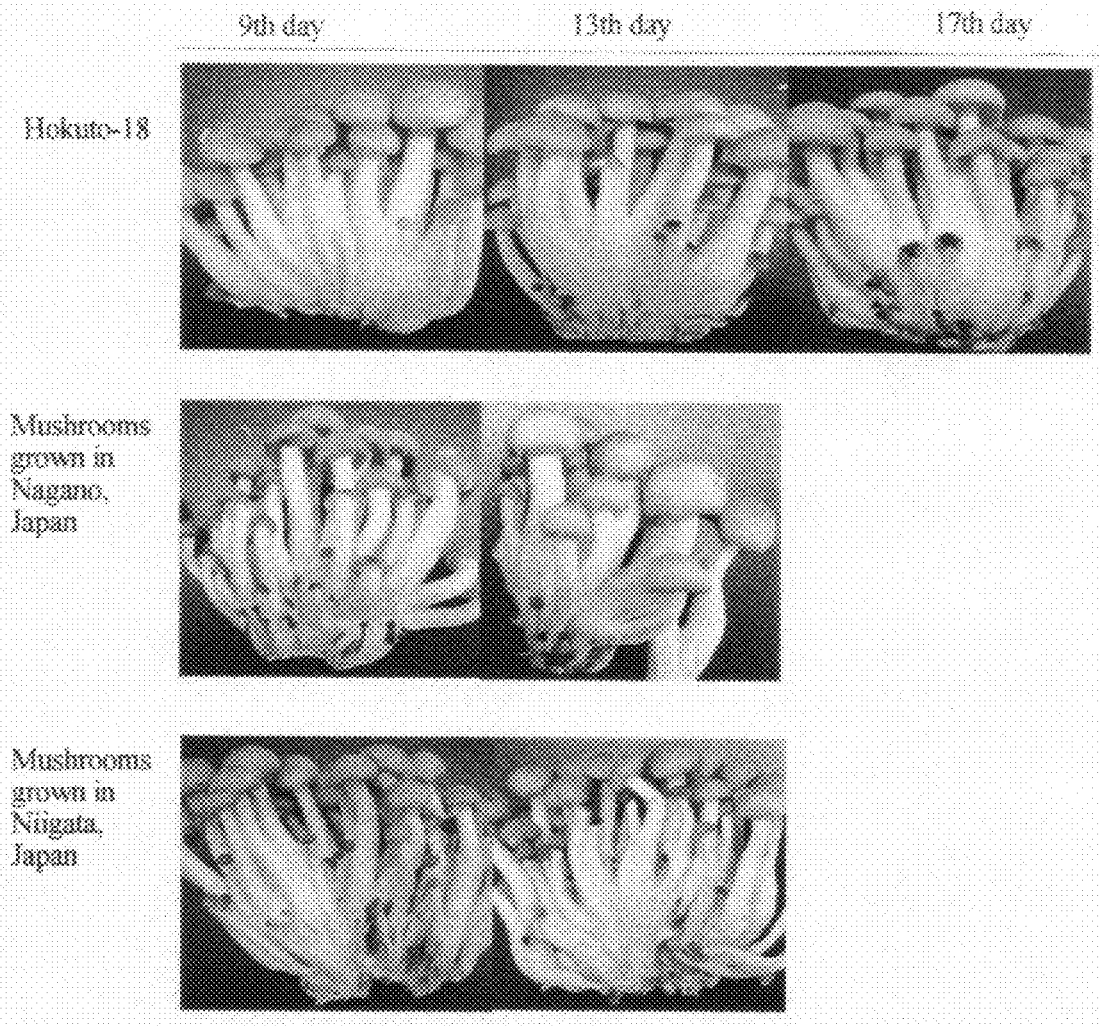
FIG. 11 shows the states of the 'Hokuto-18' mushrooms of the invention and control varieties grown in Nagano and Niigata of Japan, each on the 9th, 13th and 17 days of growing.

The differences in growth of fungal hyphae among the new variety 'Hokuto-18' and control varieties 'Hokuto-8' and 'Hokuto-16' are shown in Table 3 and FIG. 10.

TABLE 3

Differences in growth of fungal hyphae

Measurement of growth of the fimgal threads at intervals of 5° C. (mm/day)

| | Temperature (° C.) | | | | | | |
|---|---|---|---|---|---|---|---|
| Strain Name | 5 | 10 | 15 | 20 | 25 | 30 | 35 |
| 'Hokuto-18' | 0.7 | 1.3 | 2.0 | 3.1 | 3.7 | 2.5 | 0.0 |
| 'Hokuto-6' | 0.7 | 1.3 | 1.9 | 3.0 | 4.1 | 2.9 | 0.0 |
| 'Hokuto-8' | 0.7 | 1.4 | 2.0 | 3.3 | 3.9 | 2.6 | 0.0 |

Analysis of optimum temperature

| Strain Name | Temperature (° C.) | Growth of fungal threads (mm) |
|---|---|---|
| 'Hokuto-18' | 24.2 | 3.7 |
| 'Hokuto-6' | 25.0 | 4.1 |
| 'Hokuto-8' | 24.2 | 3.9 |

(4) Eating-quality characteristics (Table 4)

Figure 12:
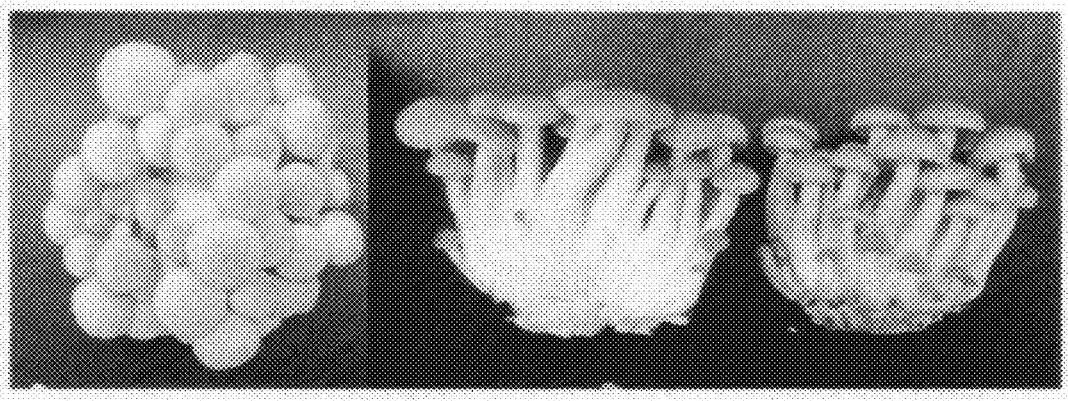
FIG. 12 shows a comparison of 'Hokuto-18' to control varieties.
Figure 12:
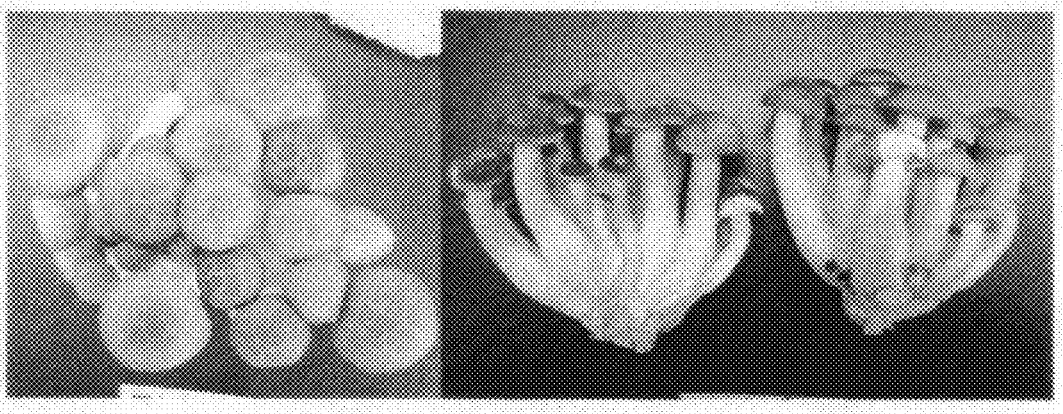
Figure 12:
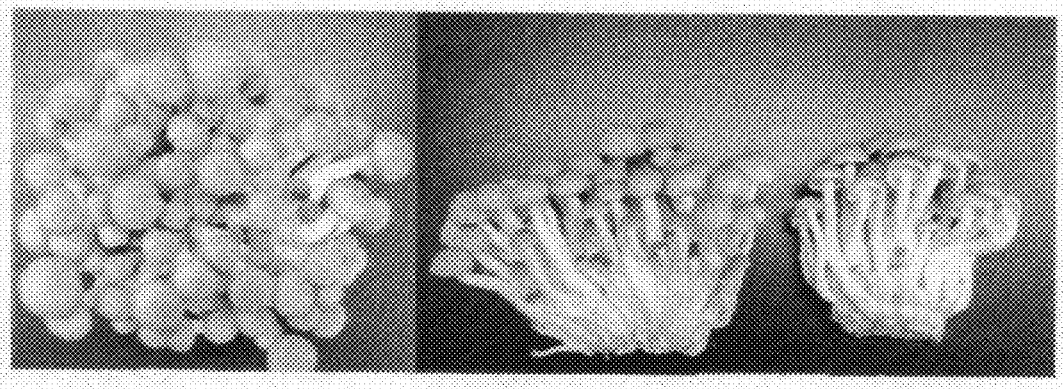

The new variety 'Hokuto-18' was compared in eating-quality characteristics with control varieties available in the market. The new variety 'Hokuto-18' and the control varieties are shown in FIG. 12.

First, Bunashimeji mushroom samples each having a fruit body of 100 grams were heated in a microwave oven (500W) for 70 minutes, and then, cooled at room temperature. Thereafter, blind tasting tests were conducted among 30 tasting testers to confirm the taste of the new variety 'Hokuto-18' compared to the control varieties available in the market with respect to daintiness, bitterness and firmness. The result of the tasting tests is shown in Table 3. As is evident from the tasting result, the new variety 'Hokuto-18' was assessed by almost all of tasting testers as delicious, not bitter and pleasingly crunchy compared to the control varieties.

TABLE 4

| | Numbers of testers who made valuations of the varieties | | | | | |
|---|---|---|---|---|---|---|
| | Daintiness | | Bitterness | | Firmness | |
| | Good | No good | Bitter | Not bitter | Crunchy | Not crunchy |
| 'Hokuto-18' | 30 | 0 | 2 | 28 | 22 | 8 |
| Nagano-grown variety | 16 | 14 | 14 | 16 | 12 | 18 |
| Niigata-grown variety | 24 | 6 | 8 | 22 | 22 | 8 |

Out of 30 tasting testers, 100% appraised as delicious. 93% of the testers appraised 'Hokuto-18' as not bitter. The tasting results show that the new variety 'Hokuto-18' is deliciously flavored.

(5) Keeping quality of 'Hokuto-18' (Table 5)

Preservation tests were carried out using the new variety 'Hokuto-18' and the control varieties available in the market. The preservation tests were conducted by packaging the varieties after harvesting to prepare 20 test packs, keeping the test packs in corrugated board boxes at 8° C. for 6 days, and further preserving them at 25° C. after the 7th day. The results of the preservation tests are shown in Table 5 below, showing that the quality of the new variety Hokuto-18 could be congruously kept in quality after the 12th day of harvesting as well. Thus, the new variety 'Hokuto-18' has apparently better keeping quality than the other existing varieties available in the market.

TABLE 5

| | Aspects of varieties after harvesting | | | | | | | | | | | | |
|---|---|---|---|---|---|---|---|---|---|---|---|---|---|
| | Elapsed days after harvesting | | | | | | | | | | | | |
| | 6 | 7 | 8 | 9 | 10 | 11 | 12 | 13 | 14 | 15 | 16 | 17 | 18 |
| 'Hokuto-18' | ○ | ○ | ○ | ○ | ○ | ○ | ○ | Δ | Δ | Δ | Δ | Δ | x |
| Nagano-grown variety | ○ | ○ | ○ | Δ | Δ | Δ | Δ | x | | | | | |
| Niigata-grown variety | ○ | ○ | ○ | Δ | Δ | Δ | Δ | x | | | | | |

○: Impeccable
Δ: Abnormality occurring in one or more test
x: samples
No commercial value The results of the aforementioned preservation tests show that the new variety 'Hokuto-18' has good keeping quality.

Figure 5:
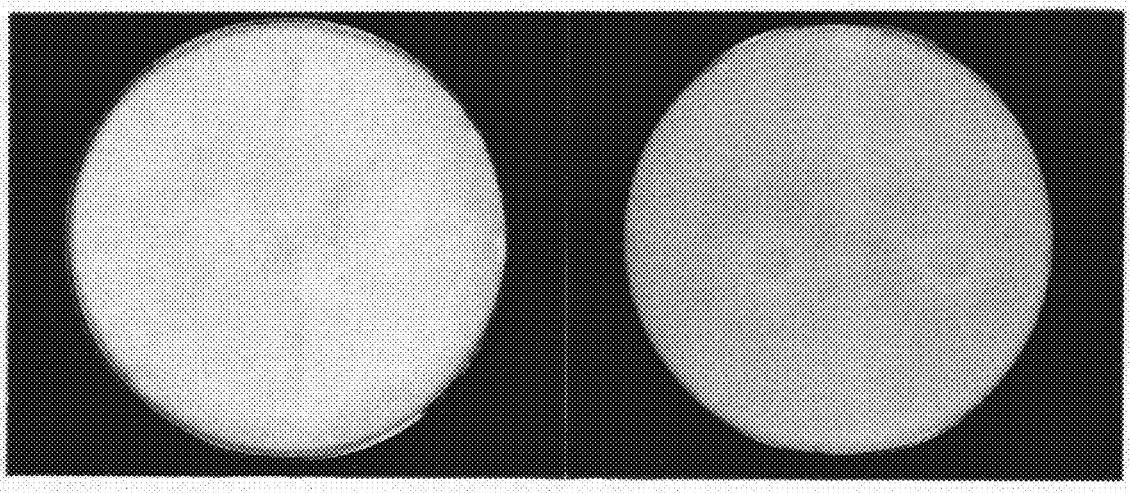
FIG. 5 shows the state of juxtapositional cultivation of the 'Hokuto-18' mushrooms placed in juxtaposition.
Figure 6:
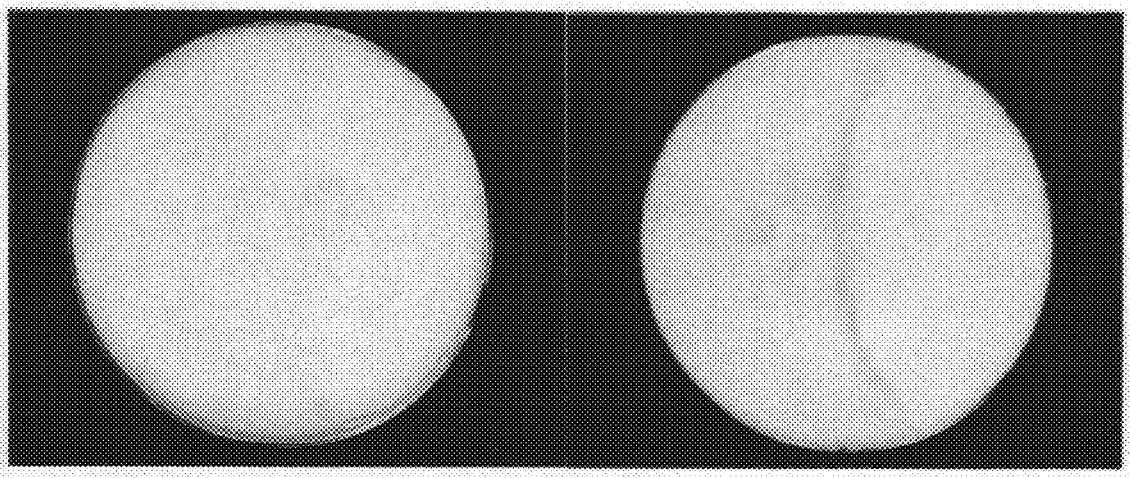
FIG. 6 shows characteristics of the 'Hokuto-18' mushrooms in cultivation.
Figure 7:
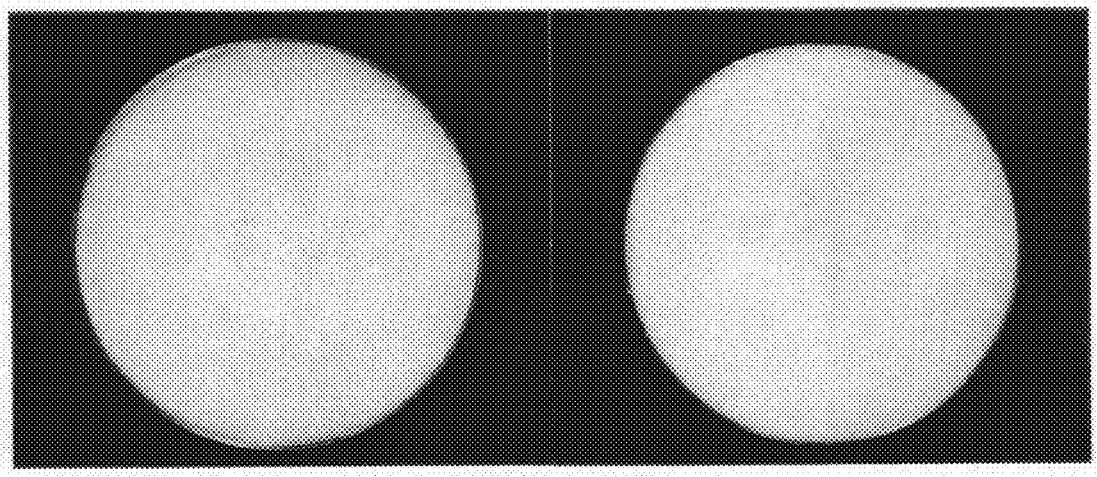
FIG. 7 shows the state of juxtapositional cultivation of the 'HOKUTO-18' mushrooms and the control variety 'Hokuto-8'.
Figure 8:
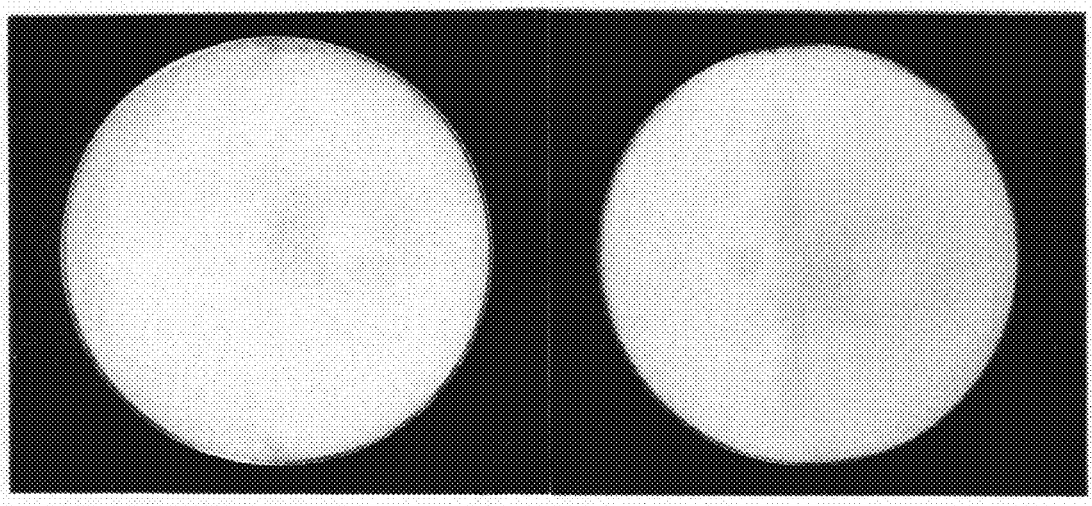
FIG. 8 shows the state of juxtapositional cultivation of the 'Hokuto-18' mushrooms and a control variety grown in Nagano, Japan.
Figure 9:
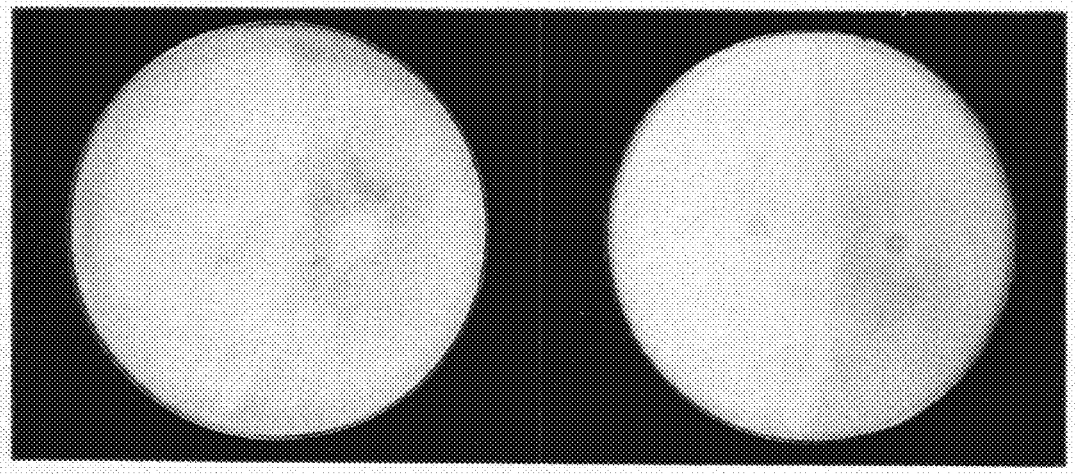
FIG. 9 shows the state of juxtapositional cultivation of the 'Hokuto-18' mushrooms and a control variety grown in Niigata of Japan.

The juxtapositional cultivations shown in FIG. 5 through FIG. 9 were made using the new variety 'Hokuto-18' of the invention, the control varieties 'Hokuto-16' and 'Hokuto-8', and commercially available mushrooms. In the juxtapositional cultivation of two 'Hokuto-18' strains of the same kind, the bacterial threads of both strains are intermingle with each other as shown in FIG. 5. However, the bacterial threads of 'Hokuto-18' take against the other control strains as shown in FIGS. 6–9. That is, the new variety 'Hokuto-18' expressly is genetically dissimilar to the existing varieties similar to 'Hokuto-18'.

As is apparent from the foregoing description, the new variety 'Hokuto-18' according to the invention is apparently distinct in morphological trait character from the other similar varieties and is exquisite in stability, reproducibility and uniformity in comparison with the existing varieties of this sort.

What is claimed is:

1. A new, distinct variety of Bunashimeji mushroom as substantially illustrated or described in the specification.

* * * * *

Hokuto-18

Mushrooms grown in Nagano, Japan

Mushrooms grown in Niigata, Japan